United States Patent [19]

Holfert et al.

[11] Patent Number: 4,976,729
[45] Date of Patent: Dec. 11, 1990

[54] ELLIPTICAL ARTIFICIAL HEART

[75] Inventors: John W. Holfert, Bountiful; Donald B. Olsen, Salt Lake City, both of Utah

[73] Assignee: University of Utah Research Foundation, Salt Lake City, Utah

[21] Appl. No.: 232,384

[22] Filed: Aug. 15, 1988

[51] Int. Cl.$^5$ .............................................. A61M 1/10
[52] U.S. Cl. ........................................ 623/3; 600/16; 600/17
[58] Field of Search ......................... 600/16, 17; 623/3

[56] References Cited

U.S. PATENT DOCUMENTS

| 3,568,214 | 3/1971 | Goldschmied | 623/3 |
| 3,656,873 | 4/1972 | Schiff | 623/3 |
| 4,376,312 | 3/1983 | Robinson et al. | 623/3 |
| 4,427,470 | 1/1984 | Kolff | 623/3 |
| 4,573,997 | 3/1986 | Wisman et al. | 623/3 |

OTHER PUBLICATIONS

"Mechanical Failures in In Vivo and in Vitro Studies of Pneumatic Total Artificial Hearts", P. A. Dew, D. B. Olsen, T. R. Kessler, D. I. Coleman, and W. J. Kolff, vol. XXX Trans. Am. Soc, Artif. Intern. Organs, 1984, pp. 112–116.

Primary Examiner—Randall L. Green
Assistant Examiner—Stephanie L. Iantorno
Attorney, Agent, or Firm—Thorpe, North & Western

[57] ABSTRACT

An artificial heart device for producing heart pumping action as part of a total artificial heart implant comprising a semi-rigid housing of approximate ellipsoidal configuration which encloses a pumping volume divided into a blood chamber and a pumping chamber by a deformable diaphragm structure which is symmetrically positioned about a short axis of the ellipsoid housing. This diaphragm structure is also configured as a hemiellipsoidal structure, allowing the device to have smaller dimensions but to maintain the required high stroke volume necessary to function within a human circulatory system. The device includes valved inlet and outlet openings coupled through the housing and in communication with the blood chamber. A pneumatic pump is coupled to the pumping chamber through a series of concentric vents formed within the base of the artificial heart device.

9 Claims, 1 Drawing Sheet

ELLIPTICAL ARTIFICIAL HEART

This invention was funded under the following grant issued by the U.S. Department of Health & Human Services: NIH R01 HL-24561.

BACKGROUND OF THE INVENTION

1. Field of Invention

This invention pertains to an artificial heart device which is implanted within the chest cavity and is powered by a pneumatic pump. More particularly, it relates to a total artificial heart which is of semi-rigid shell construction with an internal compartment divided into a blood flow chamber and a pumping chamber by means of a flexible diaphragm.

2. Prior Art

The successful extension of life utilizing the Jarvik-7 (TM) total artificial heart (TAH) offered new options for patients awaiting heart transplants. In particular, terminal patients who might have had little hope for survival because of heart transplant shortages could now hope for extended life based on the use of an artificial heart implanted within the chest cavity and powered by an external pneumatic drive system.

The Jarvik-7 TAH is characteristic of prior art devices of this type. The Jarvik-7 was fabricated from either Avcothane-51 ELASTOMER (TM) or BIOMER (TM). The basic design and construction of this artificial heart has been well documented. See for example, "The Total Artificial Heart" by R. K. Jarvik, *Scientific American* 244:66 (1981). This TAH introduced the seamless blood contacting surface for ventricles, with a multi-layered diaphragm including (i) a blood contacting diaphragm as part of the ventricle wall, and (ii) multiple pumping diaphragm structures which respond to the inflation and deflation forces of the pneumatic drive system.

A major problem of the prior art TAH structure is the difficulty of fitting the shell and attached valving and tubing within the small space typically occupied by a natural heart. The large size of the TAH made implantation particularly difficult for the surgeon who was required to perform difficult suturing of connector valves at various attachment points of the circulatory system. Failure to achieve properly sutured junctions could encourage fatal thrombogenesis.

The geometric configuration of the Jarvik-7 was a circular structure whose minimum radius and depth were limited by the need for maintaining a desired stroke volume of 100 cc. This stroke volume represents the quantity of blood which can be displaced through the TAH with full displacement of the diaphragm as part of a pumping cycle.

For the Jarvik-7, a 100 cc stroke volume was realized for left and right ventricle devices having dimensions as shown in the following table.

TABLE 1

|  | LEFT | RIGHT |
|---|---|---|
| Height | 3.555" | 3.435" |
| Width | 3.400" | 3.350" |
| Length | 3.450" | 4.010" |
| Diaphragm Height | 1.050" | 1.050" |

Because of the size limitation and space requirement for the Jarvik-7, implantation of such a TAH in patients less than 200 pounds was unrealistic. What was needed, therefore, was a TAH which was smaller in geometric configuration to allow implantation in smaller individuals, but which would maintain a sufficient stroke volume to meet patient needs.

OBJECTS AND SUMMARY OF THE INVENTION

It is an object of the present invention to provide a TAH which maintains the required stroke volume, yet occupies less spacial volume within a chest cavity.

It is a further object of this invention to provide a geometrically-shaped TAH which has an improved configuration for easier manipulation within the small space available within a chest cavity during suturing and implantation.

These and other features are realized in a total artificial heart which comprises a rigid housing having an approximate ellipsoidal configuration and enclosing a pumping volume of sufficient capacity to sustain adequate blood flow within a living being during operation, said housing being substantially symmetrical about its short axis. A deformable diaphragm structure is attached at its perimeter to an interior housing surface approximately at the largest perimeter of the pumping volume and in a symmetrical orientation about the short axis. This deformable diaphragm forms a deformable partition dividing the pumping volume into a blood flow chamber and a drive chamber and has a hemi-ellipsoidal configuration when either extended at the end of systole or diastole. Valved inlet and outlet means are coupled through the housing in communication with the blood flow chamber for attachment in line with the circulatory system of the living being and in a flow configuration which is comparable to one of the ventricles of a natural heart. Means are also provided for actuating alternate extension and collapse of the diaphragm structure with respect to the drive chamber in a recurring pumping manner to alternately expel and infuse blood from and to the blood chamber in a manner comparable to the pumping action of a natural heart.

Other objects and features of the present invention will be apparent to those skilled in the art in view of the following detailed description, taken in combination with the accompanying drawings.

DESCRIPTION OF DRAWINGS

FIG. 6 shows a cross-sectional view along the short axis of the TAH illustrated in FIG. 1.

DETAILED DESCRIPTION OF THE INVENTION

Figure 1:
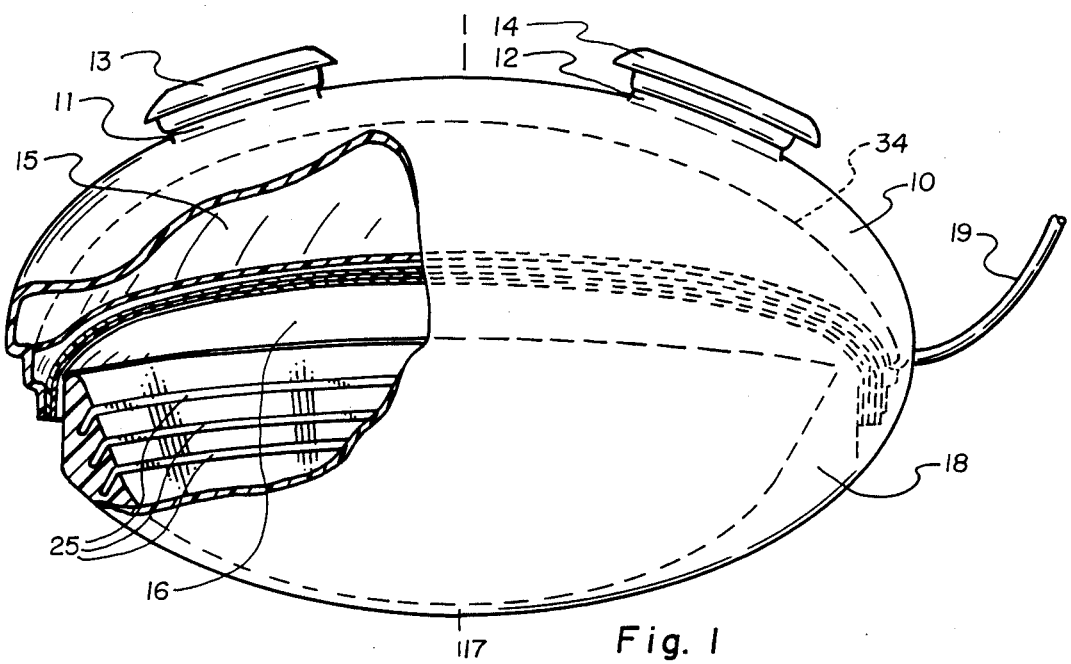
FIG. 1 shows a perspective, partial cutaway view of a total artificial heart constructed in accordance with the present invention.
Figure 2:
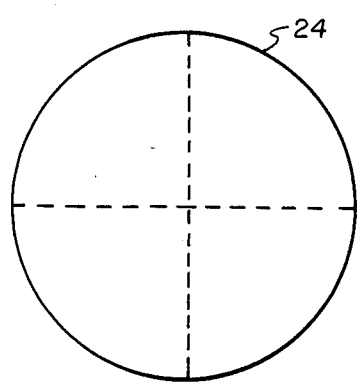
FIG. 2 graphically shows the circular construction of a prior art Jarvik-7 total artificial heart.
Figure 3:
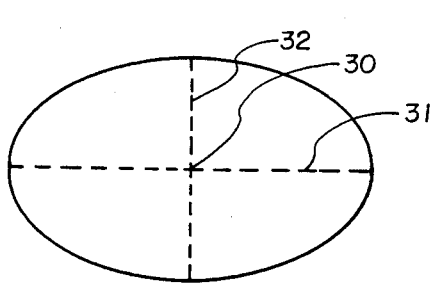
FIG. 3 illustrates the elliptical configuration of the present TAH.

FIG. 1 shows a TAH whose geometrical configuration has been structured in an elliptical form as shown in FIG. 3, as opposed to the circular form 24 (FIG. 2) of the prior art Jarvik-7 TAH. It has been discovered that adopting an ellipsoid shape, particularly for the diaphragm, enables much improved usage of available space within the chest cavity. For example, whereas the displacement volume for the left ventricle of the Jarvik-7 heart was 290 cc in order to produce a 100 cc stroke volume, the elliptical shape reduces the required displacement volume to 240 cc. The height is reduced from 3.050 inches to 2.675 inches and the width and length have been reduced from an approximate radius of 3.4 inches for the Jarvik-7 spherical shape, to a width of 2.710 inches and a length of 3.730 inches. The elliptical shape enables development of 100 cc stroke volume with a diaphragm height of only 0.850 inches, as compared to the Jarvik-7 diaphragm height of 1.050 inches.

These much smaller dimensions translate into greater working space for the physician, as well as increased capacity to implant the TAH in smaller patients. Whereas the Jarvik-7 was substantially limited to persons over 200 pounds, the present invention is capable of implantation in much smaller individuals.

Corresponding reductions in dimensions have been achieved in the right ventricle, as set forth in comparison in the following table.

TABLE 2

| Dimensional Properties of Right Ventricle | | |
|---|---|---|
| | Jarvik-7 | Ellipsoid Heart |
| Stroke Volume | 100 cc | 100 cc |
| Displacement Volume | 305 cc | 245 cc |
| Height | 3.435" | 2.775" |
| Width | 3.350" | 2.720" |
| Length | 4.010" | 3.760" |
| Diaphragm Height | 1.050" | 0.850" |

Figure 1A:
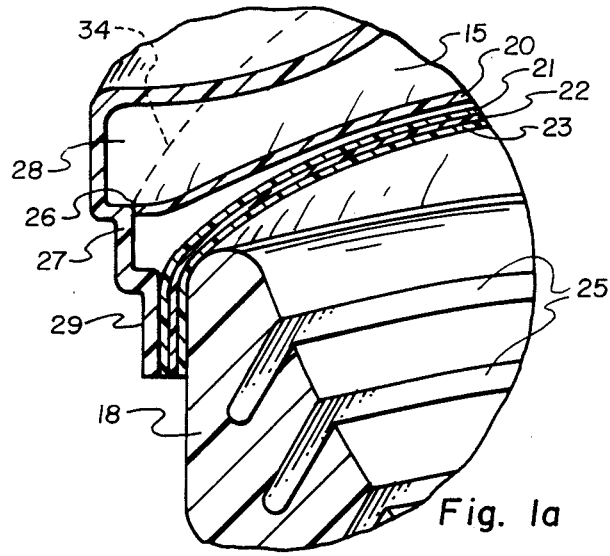
FIG. 1a shows an enlarged section of the TAH illustrated in FIG. 1.

FIGS. 1 and 1a illustrate the components making up the present invention. This TAH includes a stiff shell structure 10 which is typically fabricated of LYCRA (TM), Cardiothane (TM) or PELLETHANE (TM). Although not shown, this polymer shell may be reinforced with a dacron mesh or other appropriate fabric.

At an upper side of this semi-rigid body are positioned valued inlet and outlet means comprising the respective connectors 11 and 12 which include a collar of ISOPLAST (TM) 13 and 14 to enable suturing at points of connection within the circulatory system of the patient. Appropriate flow control valves may be positioned within each collar or connector to maintain unidirectional blood flow. Various forms of connectors and valves are well known within the industry and need no further explanation to facilitate practice of the present invention.

The interior of the subject TAH is divided into two chambers, a blood chamber 15 and a pumping chamber 16. These respective chambers and the total volume of the interior of the TAH are configured to provide a pumping volume of sufficient capacity to sustain adequate blood flow within the living body during operation of the device. Generally, this semi-rigid housing 10 will be substantially symmetrical about the short axis 17 of the ellipsoid, which corresponds to an axis perpendicular to the plane of FIG. 3 and intersecting at point 30, the intersection of reference lines 31 and 32.

The blood chamber 15 is isolated from the pumping chamber 16 by a series of four diaphragm members 20, 21, 22 and 23. Diaphragm 20 is the blood diaphragm which is configured as a seamless wall for the blood chamber 15. This seamless configuration is essential to prevent thrombogenesis as blood circulates through the TAH in response to pumping action of the respective diaphragms 20, 21, 22 and 23. This blood diaphragm 20 is composed of approximately 99% BIOMER (TM) and provides a continuous and seamless blood sac defining the blood chamber 15. This diaphragm 20 is approximately 0.006 inches thick.

The remaining diaphragms 21, 22 and 23 form an air diaphragm system which are activated by an pneumatic pump which communicates to the pumping chamber 16 through inlet tube 19. This inlet tube communicates to an opening (not shown) at the base 18 of the TAH housing 10. Air pressure travels through the tube, through a port leading to a series of air channels 25 which uniformly distribute air pressure and suction across the base 18 of the device. Each diaphragm of the air diaphragm system is similarly constructed of BIOMER (TM) and is separated from each adjacent diaphragm by a thin layer of graphite lubrication. Such lubrication is necessary to prevent the diaphragms from being torn by reason of friction as diaphragm surfaces are brought in contact in response to the changing air pressure within the pumping chamber 16. The combination of blood diaphragm and the air diaphragm system form a deformable diaphragm structure which is attached at its perimeter 26 to an interior housing surface 27 at a locus of points which approximately form the largest perimeter of the pumping volume symmetrically about the vertical axis 17.

A key feature of the present invention is the ellipsoidal shape of the diaphragm structure, made up of the respective hemi-ellipsoidal diaphragm members 20, 21, 22 and 23. This hemi-ellipsoidal configuration is observed when the diaphragm structure is fully extended at the end of either systole or diastole.

Referring to FIG. 1a, it may be noted that the blood diaphragm 20 is attached at its perimeter 26 to a separate location from the remaining diaphragm members 21, 22 and 23. The reason for such difference in attachment is the development of the seamless or continuous blood sac providing the blood contacting surface of the blood chamber 15. This surface is represented as item 28 in FIG. 1a, and extends continuously throughout the blood chamber on all wall and interior housing surfaces. The remaining diaphragm members 21, 22 and 23 are sandwiched between the side wall 29 of the upper TAH shell structure and the base 18. Because these diaphragm members are not in contact with blood, their means of attachment is not as critical.

Figure 4:
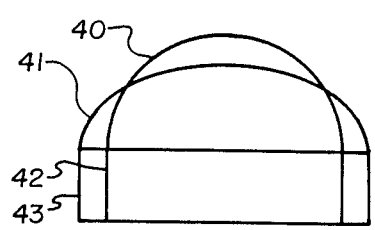
FIG. 4 graphically illustrates overlapping side views of the molds for diaphragms used in the prior art Jarvik-7, (shown in phantom line) and present TAH devices.
Figure 5:
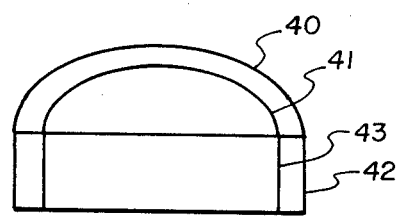
FIG. 5 shows an overlapping end view of the respective molds illustrated in FIG. 4.

FIGS. 4 and 5 show views at the side (FIG. 4) and end (FIG. 5), of overlapping molds for the respective diaphragms on the Jarvik-7 (shown in phantom line) and the present invention 41. It will be noted that the Jarvik-7 configuration is approximately hemispherical, whereas the present invention is clearly elliptical at the side view and end view. The curved upper surface of each part of FIGS. 4 and 5 represent the actual mold surfaces which provide the support for formation of the diaphragms. The base portion 42 and 43 of each respective mold are not coated. The method of fabrication for each diaphragm is by conventional technique, applying the liquid polymer over the mold surface.

The substantial difference in size and reduced volume of the device is reflected in this comparison represented by FIGS. 4 and 5. It should be clear that the smaller size of the elliptical structure would be easier to implant and require less space, enabling its use for much smaller persons than prior art devices. Despite these reduced dimensions, the present invention still meets the desired 100 cc stroke volume.

This diaphragm structure 20, 21, 22 and 23 is activated by air pressure which feeds through the air duct 19 into the base 18 of the TAH. The actual venting location for pressurized air is dispersed through a series of concentric rings providing air vent grooves 25. This dispersed pattern of pressurized air gives a more quick and timely response within the diaphragm, as well as protects the diaphragm from excessive wrinkling and consequential strain and wear.

In the present embodiment, the base 18 is formed of a polycarbonate material such as LEXAN (TM). The concentric grooves are about 0.125 inches in width and range in depth from 0.125 inches at the outer edge grooves down to 0.040 at grooves more centrally located within the base structure 18.

Operation of the elliptical structure is substantially similar to that of the earlier Jarvik-7 system. As indicated above, air pressure provided by a pneumatic source (not shown) is supplied through tube 19 into the base and through the concentric air vent grooves 25. With increased pressure, the diaphragm structure 20, 21, 22 and 23 deforms upward and continues to expand, driving blood from the blood chamber 15 as the diaphragm reaches toward its extreme limit, fully extended upward in the semi-elliptical shape as shown by dashed line 34. This occurs at the end of systole. The pneumatic source then applies a negative pressure, sucking the diaphragm toward the base position by venting air which passes through the concentric grooves 25. At the end of diastole, the diaphragm structure virtually rests against the base structure 18. This draws blood through one of the valved inlets 11 or 12. This cycle is repeated in accordance with standard pumping action within the circulatory system.

The illustrated embodiment is to be viewed as an example of the present inventive concept, and is not to be considered limiting except in accordance with the following claims.

I claim:

1. An artificial heart device for producing heart pumping action as part of a total artificial heart implant, said device comprising a semi-rigid housing of substantially ellipsoidal configuration, having elliptical cross sections at both its long and short axes and enclosing a pumping volume of sufficient capacity to sustain adequate blood flow within a living being during use, said housing having an interior surface and upper and base portions and being substantially symmetrical about its short axis;

deformable diaphragm structure attached at its perimeter to said interior housing surface approximately at the largest perimeter of the pumping volume and symmetrically about the short axis to form a deformable partition dividing the pumping volume into a blood chamber and a drive chamber, said diaphragm structure having an hemi-ellipsoidal configuration when fully extended at the end of either systole or diastole;

inlet and outlet means coupled through the housing in communication with the blood chamber for attachment in line with the circulatory system of the living being and in a flow configuration comparable to one of the two ventricles of a natural heart; and means for actuating alternating extension and collapse of the diaphragm structure with respect to the drive chamber in a recurring pumping manner to alternately expel and infuse blood from and to the blood chamber in a manner comparable to the pumping action of a natural heart.

2. An artificial heart device as defined in claim 1, wherein the diaphragm structure comprises a plurality of diaphragm members each of said diaphragm members having an interior and exterior surface and joined individually at their periphery to the interior housing surface at separated perimeter locations, one diaphragm comprising a blood diaphragm and being exposed at its interior face to the blood chamber, another diaphragm comprising a pumping diaphragm having its exterior face exposed to the pumping chamber.

3. An artificial heart device as defined in claim 2, wherein the pumping diaphragm is attached at its periphery to the interior housing face, such that the attached periphery projects approximately parallel with the short axis at its point of attachment.

4. An artificial heart device as defined in claim 2, wherein the blood diaphragm is attached at its periphery to the interior housing surface, such that the attached periphery projects toward the short axis during displacement of the diaphragm structure toward said base section of the artificial heart toward the end of diastole.

5. An artificial heart device as defined in claim 3, comprising a plurality of pumping membranes in stacked configuration.

6. An artificial heart device as defined in claim 5, wherein three pumping diaphragms are provided, each separated from an adjacent diaphragm by lubricant.

7. An artificial heart device as defined in claim 1, wherein the blood diaphragm is configured as a seamless blood contacting surface for the interior of the blood chamber.

8. An artificial heart device as defined in claim 1, wherein the means for actuating pumping action of the diaphragm structure comprises a pneumatic pumping system.

9. An artificial heart device as defined in claim 1, wherein the housing has an elliptical length of approximately 3.7 inches and an elliptical width of approximately 2.7 inches, the height of such elliptical structure being approximately 2.7 inches.

* * * * *